United States Patent

Simon et al.

[11] Patent Number: 5,993,793
[45] Date of Patent: Nov. 30, 1999

[54] USE OF SUCCINIC ANHYDRIDE DERIVATIVES IN SKIN CLEANSING COMPOSITIONS

[75] Inventors: Pascal Simon, Vitry Sur Seine; Eric Bollens, Nogent Sur Marne, both of France; Didier Gagnebien, Westfield, N.J.

[73] Assignee: L'Oreal, Paris, France

[21] Appl. No.: 08/878,765

[22] Filed: Jun. 19, 1997

[30] Foreign Application Priority Data

Jun. 21, 1996 [FR] France .................................. 96-07777

[51] Int. Cl.$^6$ ....................................................... A61K 7/02
[52] U.S. Cl. .................................... 424/70.31; 424/70.19; 510/119; 510/137; 510/158; 510/159
[58] Field of Search .................................. 428/401, 70.31, 428/70.19, 70.11, 484, 486; 510/136, 137, 158, 159, 119

[56] References Cited

U.S. PATENT DOCUMENTS 5,179,128   1/1993   Lyle et al. .

FOREIGN PATENT DOCUMENTS

| 0 107 199 A2 | 10/1980 | European Pat. Off. . |
| 0210642 | 2/1987 | European Pat. Off. . |
| 2 131 820 | 6/1984 | United Kingdom . |
| WO 94/00508 | 1/1994 | WIPO . |
| WO-A-9411333 | 5/1994 | WIPO . |
| WO-A-9535088 | 12/1995 | WIPO . |
| WO-A-9625384 | 8/1996 | WIPO . |

*Primary Examiner*—Edward J. Webman
*Attorney, Agent, or Firm*—Finnegan, Henderson, Farabow, Garrett & Dunner, L.L.P.

[57] ABSTRACT

The invention relates to the use, in cosmetic compositions for cleansing and/or removing make-up in particular from the skin, mucous membranes, eyes, and/or the hair, of at least one succinic anhydride derivative corresponding to one of the formulae I and II:

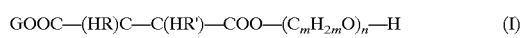

$$GOOC-(HR)C-C(HR')-COO-(C_mH_{2m}O)_n-H \quad (I)$$

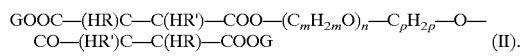

$$GOOC-(HR)C-C(HR')-COO-(C_mH_{2m}O)_n-C_pH_{2p}-O-CO-(HR')C-C(HR)-COOG \quad (II).$$

18 Claims, No Drawings

USE OF SUCCINIC ANHYDRIDE DERIVATIVES IN SKIN CLEANSING COMPOSITIONS

The invention relates to the use, as surfactants, of products derived from the condensation of alkylsuccinic or alkenylsuccinic anhydride derivatives with polyoxyalkylenes, for removing make-up and cleansing the skin, the hair and the mucous membranes.

Users expect a make-up-removing composition to be able to remove all kinds of make-up products: lipstick, powder, eyeshadow, foundation, and the like, without damaging the skin, and leaving the skin clean and soft.

Among make-up-removing products, many have aqueous bases: aqueous, aqueous-alcoholic or aqueous-glycolic lotions, transparent aqueous gels. These products contain dissolved surfactants which remove the make-up by placing the make-up products in suspension. These surfactants should be efficient at removing make-up and be of suitable tolerance and they should provide the formula with good stability.

Usually, an effective surfactant, such as, for example, a surfactant of the anionic category, is poorly tolerated. In contrast, a mild surfactant, such as, for example, a nonionic surfactant, often has an insufficient detergent activity. Better efficiency at removing make-up may be sought by increasing the amounts of surfactant in the composition, but there is then a risk of coming up against stability problems: recrystallization, coloration, poor light-stability and temperature-stability. There is thus a need to have available a relatively non-irritant and thus nonionic surfactant which however possesses good make-up-removing properties at low concentration.

The emulsifying and dispersing properties of products derived from the condensation of alkylsuccinic derivatives with polyoxyalkylenated derivatives is known from PCT application WO 94/00508. These nonionic surfactants are reputed to be of very good biodegradability.

Moreover, it is known from PCT applications WO-95/35088 and WO-94/10971 to use, in skin care, products derived from the condensation of alkylsuccinic or alkenylsuccinic derivatives with polyoxyethylenated derivatives. The products described in these documents have skincare properties which make them comparable with ceramides (treatment of dry, damaged or elderly skin, improvement of the flexibility of the stratum corneum, retention of water by the skin) and are moreover more soluble than ceramides in cosmetic compositions.

However, there was previously no indication to suggest that the compounds described in these documents could possess any cleansing and/or make-up-removing properties on the skin, mucous membranes, semi-mucous membranes and/or the hair.

Thus, the inventors have discovered, surprisingly, that certain surfactants derived from the condensation of alkylsuccinic or alkenylsuccinic anhydride derivatives with polyoxyalkylenes can be used successfully in cosmetic compositions for removing make-up from the skin and cleansing the skin and the hair. These surfactants are efficient at removing make-up and cleansing, allied with great softness, and they allow formulations to be obtained which are stable for a long time. Furthermore, they may be used alone or in combination with other common surfactants.

A subject of the invention is thus the use, in cosmetic compositions for cleansing and/or removing make-up from the skin, mucous membranes, semi-mucous membranes and/or the exoskeleton, such as the hair, of at least one succinic anhydride derivative corresponding to one of the formulae I and II:

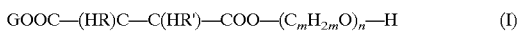
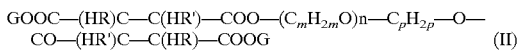

in which:

one of the radicals R and R' is a linear or branched $C_6$–$C_{22}$ alkyl or alkenyl radical and the other radical is a hydrogen atom;

n ranges from 2 to 100;

m is equal to 2 or 3 and may vary along the polyoxyalkylene chain;

p is equal to 2 or 3;

G is a hydrogen atom, a $C_1$–$C_6$ alkyl group, a radical —$(C_{m'}H_{2m'}O)_{n'}H$, in which n' ranges from 2 to 100 and m' is equal to 2 or 3 and may vary along the chain, or a cation, provided that when G is a radical —$(C_{m'}H_{2m'}O)_{n'}H$, then at least one among m and m' is equal to 2.

In formulae (I) and (II), n and n' are average values and are therefore not necessarily integers. A value of n ranging from 5 to 60 is advantageously chosen, and even more preferably from 10 to 30.

The compounds according to the invention comprise at least one polyoxyalkylene chain composed of oxyethylene and/or oxypropylene residues. The chain may be a homopolymeric chain of ethylene glycol residues or of propylene glycol residues or it may be a block or random copolymer containing both ethylene glycol residues and propylene glycol residues. Among the compounds comprising more than one polyoxyalkylene chain, the chains may be identical or different.

When G represents a radical —$(C_{m'}H_{2m'}O)_{n'}H$, the conditions are preferably: n=n' and m=m'.

When G is a cation, it may be selected from an ion of an inorganic or organic base such as, for example, an ion of an alkali metal, among which mention may be made of Na+ or K+, or the quaternary ammonium ion, or a basic salt of lysine or of arginine.

G preferably represents a hydrogen atom.

The radical R or R' which is other than H is advantageously selected from linear $C_8$–$C_{22}$ 1,2-alkylene radicals.

The compounds of formulae (I) and (II) described above may be prepared in accordance with the description which is given in patent application WO-94/00508, or in one of the patents GB-2,131,820 and EP-0,107,199, the disclosures of all of which are hereby incorporated by reference.

Another subject of the present invention is the use in a cosmetic or hygiene composition, as an agent for cleansing and/or removing make-up from the skin, mucous membranes, semi-mucous membranes and/or the exoskeleton, such as the hair, of at least one succinic anhydride derivative corresponding to one of the formulae (I) and (II) above.

Another subject of the invention is a process for cleansing and/or removing make-up from a support such as the skin, mucous membranes, semi-mucous membranes, the exoskeleton and/or the eyes, characterized in that a composition comprising at least one succinic anhydride derivative corresponding to one of the formulae (I) and (II) is applied to the said support.

The composition of the invention may be in the form of an emulsion, in particular an oil-in-water or water-in-oil emulsion, or even in the form of a multiple emulsion. It may also be in the form of an aqueous solution, which is optionally gelled, or in the form of a lotion, for example a two-phase lotion, an aqueous or aqueous-alcoholic lotion, a cream, a milk or even a foam.

The composition according to the invention may comprise a fatty phase based on animal, plant, mineral, silicone, fluoro and/or synthetic oil. The fatty phase may also comprise fatty alcohols or fatty acids, as well as surfactants.

Mention may be made in particular of hydrocarbon oils such as liquid paraffin or liquid petrolatum; perhydrosqualene; arara oil, sweet almond oil, calophyllum oil, palm oil, castor oil, avocado oil, jojoba oil, olive oil or cereal germ oil; alcohols such as oleyl alcohol, linoleyl or linoleneyl alcohol, isostearyl alcohol or octyldodecanol. Mention may also be made of silicone oils such as polydimethylsiloxanes (PDMSs), which are optionally phenylated, such as phenyltrimethicones.

The fatty phase may also comprise a make-up-removing oil such as fatty acid ester, in particular the esters obtained from a straight- or branched-chain alcohol having from 1 to 17 carbon atoms and from a straight- or branched-chain fatty acid having from 3 to 18 carbon atoms.

Such an ester may be selected in particular from dioctyl adipate, 2-ethylhexyl palmitate, diisopropyl adipate, 2-ethylhexyl hexanoate, ethyl laurate, methyl myristate, octyldodecyl octanoate, isodecyl neopentanoate, ethyl myristate, myristyl propionate, 2-ethylhexyl 2-ethylhexanoate, 2-ethylhexyl octanoate, 2-ethylhexyl caprate/caprylate, methyl palmitate, butyl myristate, isobutyl myristate, ethyl palmitate, isohexyl laurate, hexyl laurate and isopropyl isostearate.

The fatty phase may be present in a proportion of 5–95% by weight in the case of an emulsion.

The composition according to the invention may also comprise an agent which allows the fatty phase to be placed in suspension, for example, a copolymer of $C_{10}$–$C_{30}$ alkyl acrylates and of acrylic or methacrylic acid or of their ester (Pemulen TR1, Pemulen TR2, Carbopol 1342 from Goodrich); or an acrylamide/methylpropanesulphonic acid copolymer (Sepigel from Seppic), and/or an agent for placing the fatty phase is dispersion, such as an emulsifying system or a vesicle system based on vesicles, which are optionally of nanometric size, being made up of ionic lipids (liposomes) or nonionic lipids, and in particular the emulsifying systems which are well known to those skilled in the art, made up of glyceryl stearate/PEG 100 stearate (CTFA), of cetyl alcohol and of stearyl alcohol.

The composition of the invention may also comprise an agent for modifying its viscosity and for obtaining more or less gelled textures, such as:

cellulose derivatives, such as carboxymethylcellulose, hydroxyethylcellulose, or hydroxypropylmethylcellulose, natural gums such as xanthan gum, guar gum and carob gum, scleroglucans, chitin derivatives, chitosan derivatives and carrageenans, polycarboxyvinyl derivatives of the Carbomer type, sold by Goodrich under the names Carbopol, 940, 951 and 980, or by 3V-Sigma under the name Synthalen K or Synthalen L.

The composition according to the invention may also comprise, in a known manner, adjuvants commonly used in the field considered, such as preserving agents, antioxidants, fragrances, fillers such as kaolin, starch, or hollow microspheres, pigments, UV screening agents, sequestering agents, essential oils, dyestuffs, hydrophilic or lipophilic active agents such as hydrating agents, in particular glycerol, butylene glycol, antiinflammatory agents such as allantoin, bisabolol, anti-free-radical agents such as vitamin E or derivatives thereof, calmants such as cornflower water, extract of iris, depigmenting agents, biological active agents such as urea, amino acids, vitamins and derivatives thereof, proteins, salicylic acid and derivatives thereof, a-hydroxy acids, pyrrolidonecarboxylic acid and salts thereof, and ceramides.

A person skilled in the art will take care to select this or these optional additional compounds and/or the amount thereof such that the advantageous properties of the composition according to the invention are not, or are not substantially, adversely affected by the addition envisaged.

The composition according to the invention is preferably in the form of an optionally gelled aqueous solution, a two-phase lotion, a simple aqueous lotion or an aqueous-alcoholic lotion. These forms do not require the use of other surfactants to stabilize them and they are better tolerated by all skin types, in particular sensitive skins.

The composition preferably has a pH which respects the skin, generally one of from 5 to 8, preferably a pH of 5.5 to 7.5.

The compositions according to the invention find particular use as make-up-removing milk or lotion for the eyes and/or the skin, in particular facial skin, and also as shampoo and/or shower gel.

Examples of formulae are given below and these allow the invention to be illustrated without limiting its scope.

In all these examples, the percentages are given by weight.

The amounts are evaluated as active material.

Compounds E1, E2 and E3 used in these examples are prepared in accordance with Examples 1 to 3 of patent EP-0, 107, 199

Preparation of Compound E1 pursuant to Example 1 of EP 107,199

22.4 g nonenyl-succinic acid anhydride was warmed up to 90° C. with constant mixing. 150.0 g polyethylene glycol 1500 (x=34) was added to it in drops over 30 minutes, then stirred for a full hour at a temperature of 90° C. When cooled, the mixture yielded E1 (see below): Acid no.: 31.5 mg KOH/g, HLB: 15.0.

Preparation of Compound E2 pursuant to Example 2 of EP 107,199

167 g dodecylpolyglycolether (x=13, OH: 66–69 mg KOH/g) and 20 g succinic acid anhydride were reacted at 90° C. for one hour. When cooled to room temperature, the mixture yielded E2 (see below): Acid no.: 59–61 mg KOH/g, HLB:12.

Preparation of E3 pursuant to Example 3 of EP 107,199

22.4 g nonenyl-succinic acid anhydride was warmed up to 90° C. with constant mixing. 29.0 polyethylene glycol 300 (x=7) was added to it in drops over 30 minutes, and the mixture was stirred for a full hour at a temperature of 90° C. When cooled, the mixture yielded E3: Acid no.: 106–109 mg KOH/g, HLB: 10.5.

Thus, the three compounds prepared are the following:

E1: formula (I) with R=trans-2-n-dodecylene, R'=H, m=2, n=18, G=H

E2: formula (I) with R=trans-2-n-hexadecylene, R'=H, m=2, n=18, G=H

E3: formula (II) with R=trans-2-n-hexadecylene, R'=H, m=2, n=18, P=2, G=H

EXAMPLE 1

Make-up-removing milks were prepared in the form of an O/W emulsion having the following formula:

| | |
|---|---|
| 2-Ethylhexyl palmitate | 15% |
| Compound Ei (i = 1, 2, 3) | 1.5% |
| Pemulen TR2 (Goodrich) | 0.7% |
| Triethanolamine | 0.5% |
| Preserving agent | 0.2% |
| Fragrance | 0.3% |
| Water | qs 100 |

These milks removed make-up very well without stinging around the eyes. They left the skin soft and clean.

EXAMPLE 2

Make-up-removing lotions were prepared, of formula:

| | |
|---|---|
| Compound Ei (i = 1, 2, 3) | 0.8% |
| Poloxamer 184* | 1% |
| Preserving agent | 0.15% |
| Fragrance | 0.2% |
| Water | qs 100 |

EXAMPLE 3

Compositions in accordance with the invention were prepared:

| Composition C: | |
|---|---|
| Paraben | 0.2% |
| EDTA | 0.1% |
| Compound Ei (i = 1, 2, 3) | 0.65% |
| Water | qs 100 |

A composition which had the same percentage of surfactant as the compositions Ci (i=1,2,3) according to the invention was used as control, this control composition being known for its good make-up-removing properties and comprising:

| Composition T: | |
|---|---|
| Paraben | 0.2% |
| EDTA | 0.1% |
| Sodium lauryl ether sulphate | 0.23% |
| Cocoamphodiacetate | 0.42% |
| Water | qs 100 |

A) "in vitro" Make-up-removing Power

The make-up-removing power of these compositions was checked using the technique known as the "make-up-removing robot":

the machine was composed of a plate and an arm fitted with a weight which exerted a pressure of 100 g/cm² on the plate and was equipped at one of its ends with a pad of cotton wool which slid over the plate.

a thin layer of black waterproof mascara marketed under the name "Aquacils" by the company Lancome was placed on the plate.

this plate was dried for 4 hours.

the pad of cotton wool was soaked with forty drops of the make-up-removing composition to be tested and a back-and-forth motion was carried out on the plate containing the mascara.

this operation was repeated for as long as the plate was not free of mascara, the pad of cotton wool being changed after each passage.

the number of pads of cotton wool required for complete removal of the make-up was noted.

The total absence of mascara from the plate constituted, according to this test, complete removal of make-up. Two back-and-forth motions were required in order to remove all of the mascara from the plate of the make-up-removing robot with any of the compositions Ci, as well as with the control composition T.

B) "in vitro" Make-up-removing Power

Tests of the removal of make-up from the eyes were carried out on women, on half the face: make-up was removed from half of the face with composition C2 and from the other half with the control composition T. The test was carried out on 11 individuals.

Their observations were noted: the make-up-removing power of composition C2 was superior for 60% of the individuals. These two tests show that the make-up-removing compositions according to the invention are highly efficient. These compositions avoid the use of more irritating amphoteric and anionic surfactants.

C) Ocular Tolerance

The ocular tolerance was measured by determining the LSR (Lachrymal Surface Response) parameter.

The surfactant compositions were diluted in a synthetic lachrymal liquid containing a model protein: bovine serum albumin. The curves of the variation in static surface tension of solutions as a function of the concentration of the surfactant in these solutions was recorded at a temperature of 25° C. using a Krüss K12 ring tensiometer equipped with an automatic burette. The stock solution had a concentration of 1 or 2 g/l, the initial concentration of the measurements was 20 or 50 mg/l, the final concentration was 600 or 1200 g/l, the number of points taken into account was 33.

The LSR parameter was calculated from the differential of the curve s=f(log[C]) in which s represents the surface tension and [C] represents the concentration of the surfactant in the solution. This parameter was calculated according to the formula: LSR=[f.dS/df]$_{f=f0}$ in which f represents the dilution factor.

The LSR parameter of the control solution T was 24, that of the composition C2 was less than 6, which indicated an ocular tolerance which was very much higher for this composition than for the control composition.

What is claimed is:

1. A method of cleansing and/or removing make-up from the skin, mucous membranes, semi-mucous membranes, eyes, and/or exoskeleton, said method comprising applying to said skin, mucous membranes, semi-mucous membranes, eyes, and/or exoskeleton a cosmetic or hygiene composition comprising at least one succinic anhydride derivative of the following formulae I or II:

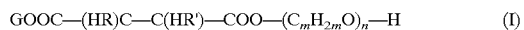
$$GOOC-(HR)C-C(HR')-COO-(C_mH_{2m}O)_n-H \qquad (I)$$

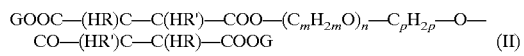
$$GOOC-(HR)C-C(HR')-COO-(C_mH_{2m}O)_n-C_pH_{2p}-O-$$
$$CO-(HR')C-C(HR)-COOG \qquad (II)$$

in which:

one of the radicals R and R' is a linear or branched $C_6$–$C_{22}$ alkyl or alkenyl radical and the other radical is a hydrogen atom;

n ranges from 2 to 100;

m is equal to 2 or 3 and may vary along the polyoxyalkylene chain;

p is equal to 2 or 3;

G is a hydrogen atom, a $C_1$–$C_6$ alkyl group, a radical —$(C_mH_{2m'}O)_{n'}H$, in which n' ranges from 2 to 100 and m' is equal to 2 or 3 and may vary along the chain, or a cation, provided that when G is a radical —$(C_{m'}H_{2m'}O)_{n'}H$, then at least one of m and m' is equal to 2.

2. A method according to claim 1, wherein said exoskeleton is the hair.

3. A method according to claim 1, wherein G represents a radical —$(C_{m'}H_{2m'}O)_{n'}H$, and n=n' and m=m'.

4. A method according to claim 1, wherein G is a cation, said cation being an ion of an inorganic or organic base, or a basic salt of lysine or of arginine.

5. A method according to claim 4, wherein said ion of an inorganic or organic base is an ion of an alkali metal, the quaternary ammonium ion, or a basic salt of lysine or of arginine.

6. A method according to claim 5, wherein said ion of an alkali metal is $Na^+$ or $K^+$.

7. A method according to claim 1, wherein G represents a hydrogen atom.

8. A method according to claim 1, wherein n ranges from 5 to 60.

9. A method according to claim 8, wherein n ranges from 10 to 30.

10. A method according to claim 1, wherein the radical R or R' which is other than H is a linear $C_8$–$C_{22}$ 1,2-alkylene radical.

11. A method according to claim 1, wherein said at least one succinic anhydride derivative is a compound of the formula:

HOOC—(HR)C—$CH_2$—COO—$(C_2H_4O)_{18}$—H with R=trans-2-n-dodecylene,

HOOC—(HR)C—$CH_2$—COO—$(C_2H_4O)_{18}$—H with R=trans-2-n-hexadecylene, or

HOOC—(HR)C—$CH_2$—COO—$(C_2H_4O)_{18}$—$C_pH_{2p}$—O—CO—$CH_2$—C(HR)—COOH with R=trans-2-n-hexadecylene.

12. A method according to claim 1, wherein the composition is in the form of an oil-in-water or water-in-oil emulsion, a multiple emulsion, an aqueous solution, a gelled aqueous solution, a lotion, a two-phase lotion, an aqueous lotion, an aqueous-alcoholic lotion, a cream, a milk or a foam.

13. A method according to claim 1, wherein the composition further comprises at least one surfactant and/or at least one make-up-removing oil.

14. A method according to claim 13, wherein the make-up-removing oil is an ester obtained from a straight- or branched-chain alcohol having from 1 to 17 carbon atoms or from a straight- or branched-chain fatty acid having from 3 to 18 carbon atoms.

15. A method according to claim 1, wherein the composition has a pH ranging from 5 to 8.

16. A method according to claim 15, wherein the composition has a pH ranging from 5.5 to 7.5.

17. A method according to claim 1, wherein the composition is a make-up-removing milk or lotion for the eyes and/or the skin, a shampoo and/or a shower gel.

18. A method according to claim 17, wherein said composition is a make-up-removing milk or lotion for facial skin.

* * * * *